United States Patent [19]

Mathews

[11] Patent Number: 5,008,203
[45] Date of Patent: Apr. 16, 1991

[54] METHOD FOR THE DETERMINATION OF OXYGEN DEMAND IN SULFUR RECOVERY INSTALLATIONS

[75] Inventor: Manfred Mathews, Bad Nauheim, Fed. Rep. of Germany

[73] Assignee: Ametek, Inc., Pittsburgh, Pa.

[21] Appl. No.: 227,772

[22] Filed: Aug. 2, 1988

Related U.S. Application Data

[63] Continuation-in-part of Ser. No. 629,172, Jul. 9, 1984, abandoned.

[51] Int. Cl.$^5$ ............................................. G01N 35/00
[52] U.S. Cl. ................................ 436/55; 436/62; 436/137; 436/143; 422/62; 423/574 R
[58] Field of Search ................ 422/62, 91, 108; 436/55, 62, 137, 127, 121, 122, 143; 423/573.1, 574 R, DIG. 5

[56] References Cited

U.S. PATENT DOCUMENTS

| | | | |
|---|---|---|---|
| 3,026,184 | 3/1962 | Karasek | 422/62 |
| 3,854,876 | 12/1974 | Rankine et al. | 422/62 |
| 3,933,992 | 1/1976 | Andral et al. | 423/573.1 |
| 4,021,201 | 5/1977 | Vautrain et al. | 423/574 R |
| 4,320,378 | 3/1982 | Taniguchi et al. | 422/98 |
| 4,351,182 | 9/1982 | Schmidberger | 422/98 |
| 4,459,275 | 7/1984 | Seike et al. | 423/574 R |

Primary Examiner—David L. Lacey
Assistant Examiner—William H. Beisner
Attorney, Agent, or Firm—Webb, Burden, Ziesenheim & Webb

[57] ABSTRACT

The invention relates to a method for monitoring and rapid predetermining of the oxygen demand for the combustion of hydrogen sulfide-containing gas mixtures which allows a quick adjustment to changing gas compositions by regulation of the oxygen supply.

2 Claims, 3 Drawing Sheets

METHOD FOR THE DETERMINATION OF OXYGEN DEMAND IN SULFUR RECOVERY INSTALLATIONS

This application is a continuation-in-part of U.S. Ser. No. 629,172 filed July 9, 1984, now abandoned.

SUMMARY

Method for the determination of oxygen demand in sulfur recovery installations. A sample of the gas mixture is completely burned and the oxygen and sulfur dioxide content in the burned sample gas mixture is determined with two continuously operating analysis instruments for the continuous monitoring and rapid predetermination of the oxygen demand in the combustion of hydrogen sulfide-containing gas mixtures. The output signals of the analysis instruments represent a measure for the oxygen demand and are used for the control of the oxygen supply to the main gas flow.

BACKGROUND OF THE INVENTION

The desulfurization of hydrogen sulfide-containing gas mixtures produced, for example, in chemical processing, gas purification or combustion installations is of great significance from an economical viewpoint—sulfur recovery—and for ecological reasons—air quality.

Desulfurization in sulfur recovery installations mostly operate according to the Claus process. With this method, part of the hydrogen sulfide is partially oxidized in a first reaction step in a combustion chamber to sulfur dioxide:

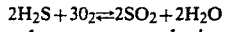

In subsequent catalytic reaction steps, the produced sulfur dioxide is converted to sulfur with non-oxidized hydrogen sulfide:

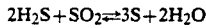

In order to set the stoichiometric ratio of $H_2S$: $SO_2 = 2:1$ required for these reaction steps an effort must be made to oxidize in the first reaction step as accurately as possible one third of the hydrogen sulfide to sulfur dioxide by means of an appropriate air supply. Since the content of hydrogen sulfide in the operation gas is, however, subject to fluctuations and, in addition, other combustible gases such as hydrocarbons may be present in varying amounts which changes the oxygen demand, the determination of the oxygen demand and the corresponding regulation of the oxygen supply is of great importance in these installations.

This is of course also applied to waste gas purification installations added to a Claus installation in which for process reasons, an $H_2S/SO_2$ ratio must be set which differs from 2. These include, for example, the "Sulfreen" process and the thermal post treatment of the Scot Process.

Many proposals were made, therefore, for regulation systems for adjusting the air/oxygen supply to the actual demand. U.S. Pat. No. 3,945,904, for example, describes a method in which the $H_2S$ and $SO_2$ content in the waste gas leaving the Claus installation is determined. To analyze these gases, titration instruments are used and their signals regulate the air supply. According to U.S. Pat. No. 4,100,266 an analysis is conducted of the $H_2S$ and $SO_2$ leaving the Claus process. Gas chromatographs are proposed here as analysis instruments and their signals are processed in a process computer and are used for the control of valves which set the desired ratio of air to hydrogen sulfide-containing gas. According to U.S. Pat. Nos. 3,985,864 and 4,021,201 an analysis of the $H_2S$ and $SO_2$ in the waste gas flow of a Claus installation takes place in a similar manner whereby the obtained signal affects the regulation system for the air supply accordingly.

All these methods, however, have the disadvantage that the regulation system can only intervene with a correction when the installation has already departed from its optimum operating condition.

In some of the described methods, for example, in the above cited U.S. Pat. Nos. 3,985,864 and 4,021,201 provisions are made, to be sure, to immediately correct changes in the pressure of the operation gas, for example, when the regulation system is connected to pressure and throughput meters but these inherently can only consider physical changes of the operation gases. Concentration changes in the operation gas, for example, a change in the hydrogen sulfide concentration, the hydrocarbon content or a change in the chemical composition of the hydrocarbons can only be detected in the waste gas analysis. These methods fail, therefore, with rapid composition changes in the operation gas.

A method is also known (U.S. Pat. No. 3,854,876) which avoids some of these problems by taking a sample of the operation gas and/or waste gas which is subjected to complete combustion in a furnace. After condensation of the water vapor and separation of all liquid and solid components in appropriate traps and filters, the carbon dioxide content is measured in a first analyzer and the sulfur dioxide content is measured in a second analyzer The gas mixture then goes through an oxygen analyzer designed as a monitor and a warning signal is emitted when a predetermined minimum oxygen content is not present. The two analyzers for carbon dioxide and sulfur dioxide content emit electrical signals corresponding to the measured $CO_2$ and $SO_2$ concentration which are processed in an analog computer and are finally used for regulating a process variable for the purpose of optimizing the sulfur recovery.

Photometers are proposed for the rapid and continuous analysis, which measure the carbon dioxide concentration by infrared absorption and the sulfur dioxide concentration by UV absorption.

But this method also has several disadvantages. The gas mixture to be analyzed must be carefully relieved of water vapor since otherwise the IR measurement of the $CO_2$ content is subject to interference. The installation of coolers, filters and liquid traps in the line system increases the time before the analysis results are available so that the regulation is also delayed. In the water vapor condensation, moreover, the part of $CO_2$ and $SO_2$ dissolved in the water escapes the measurement by the photometer. This percentage, furthermore, fluctuates with the temperature which determines the solubility. The determination of the carbon dioxide content finally does not permit a safe conclusion on the type of hydrocarbon contained in the sample gas and, therefore, on the oxygen demand of the process since saturated, unsaturated and aromatic hydrocarbons have a different oxygen demand which is not proportional to the number of carbon atoms. A carbon dioxide content in the operation gas and sample gas, moreover, falsifies the result with respect to oxygen demand.

It was, therefore, the objective of the invention to provide a method for predetermining reliably and quickly the oxygen demand of a desulfurization or sulfur recovery installation from an analysis of the operation gas mixture to detect momentarily occurring fluctuations in the composition of the operation gas and to confront these fluctuations by counter measures.

The solution of this objective consists of a method for continuously monitoring and predetermining the oxygen demand in the combustion of hydrogen sulfide-containing gas mixtures for sulfur recovery and waste gas purification by continuous sample taking of the operation gas, its complete combustion in a combustion furnace (123) with at least the stoichiometric oxygen amount and analysis of two components of the burned gas mixture in continuously operating analysis instruments with their output signals used for regulating the oxygen supply to the main gas flow and is characterized in that the analytically detected components of the burned gas mixtures are oxygen and sulfur dioxide.

BRIEF DESCRIPTION OF THE DRAWINGS

The invention is explained in more detail below by means of FIGS. 1 and 2.

DETAILED DESCRIPTION OF THE PREFERRED EMBODIMENT

Figure 1:
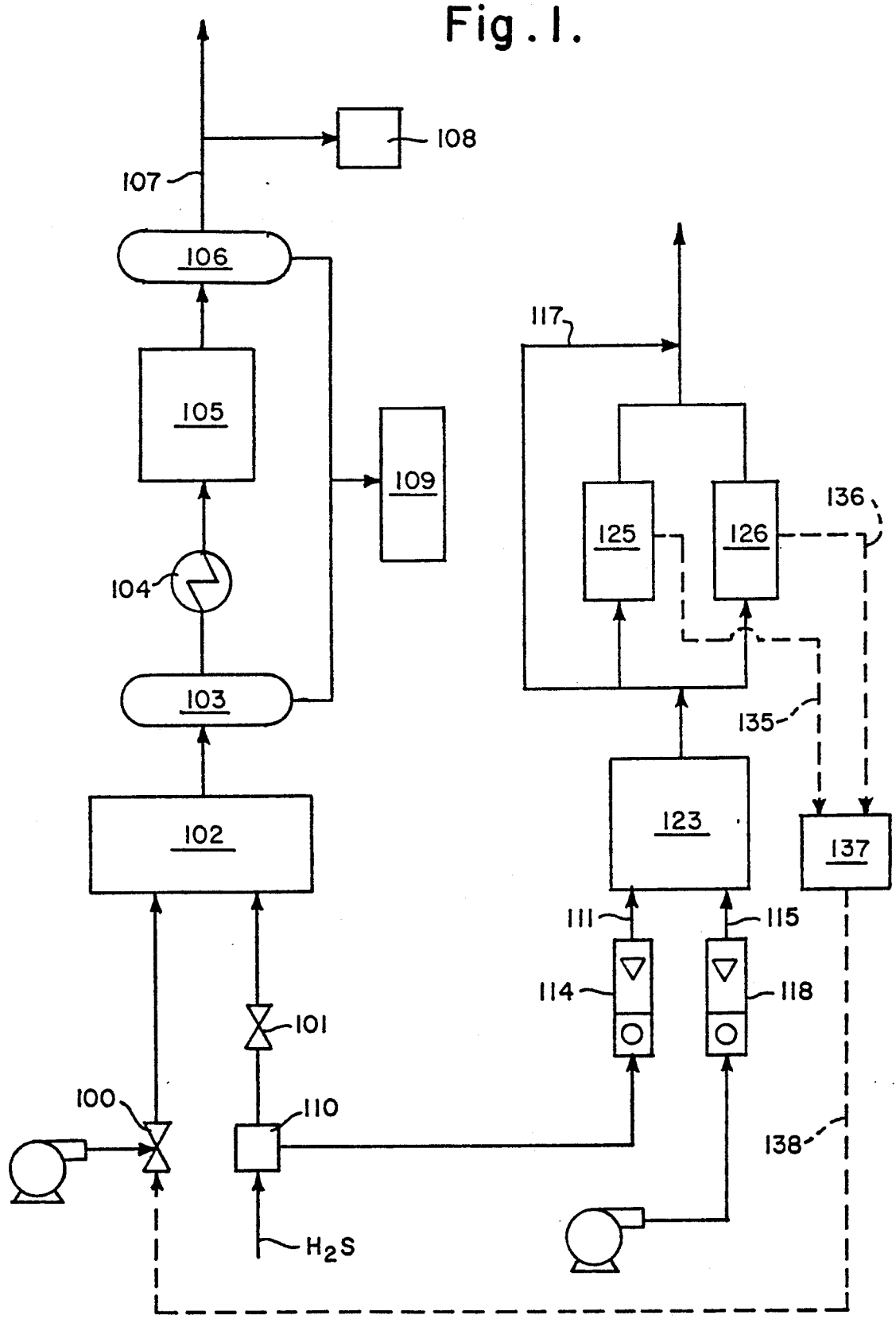
FIG. 1 shows the simplified flow diagram of a Claus installation with the integrated method of the invention and FIG. 2 shows a detailed diagram of the preferred refinement of the method of the invention.

In a desulfurization installation according to the Claus Process as illustrated schematically and simplified in FIG. 1, hydrogen sulfide-containing gas and air are supplied via control valves (101) and (100) respectively to a combustion furnace (102) in which a partial oxidation of the $H_2S$ to $SO_2$ takes place according to the reaction $6H_2S + 3O_2 \rightleftharpoons 4H_2S + 2SO_2 + 2H_2O$. In a first condenser (103), the sulfur vapor produced according to the reaction $2H_2S + O_2 \rightleftharpoons 2S + 2H_2O$ is condensed and supplied to a collecting tank (109). The $H_2S/SO_2$-containing gas mixture relieved of elementary sulfur is heated again in a heat exchanger (104) and conducted into the catalytic Claus reactor (105) in which additional sulfur is produced by the reaction $2H_2S + SO_2 \rightleftharpoons 3S + 2H_2O$. The sulfulr is separated in the condenser (106) and also supplied to the collecting tank (109). The still unconverted $H_2S$ and $SO_2$ in the gas flow (107) is converted according to the above reaction equation into sulfur in heat exchanger (not shown) and Claus reactors added to the condenser (106).

In order to determine the optimum oxygen demand according to the invention, a sample (11) defined by the throughput regulator (114) is taken from the main gas flow via the sampler (11)) and supplied to a combustion furnace (123) together with at least stoichiometric amount of air or oxygen (115) defined by a throughput regulator (11) in which furnace all combustible components of the gas mixture are completely burned to $SO_2$, $CO_2$ and $H_2O$. Preferably, an excess of air or oxygen is used. The reaction products are supplied to two selectively and continuously operating analyzers one of which (125) measures the excess oxygen and the second (126) measures the $SO_2$ concentration. The analyzers may be either arranged in parallel as shown in FIG. 1 or they may also be arranged in series as shown in FIG. 2.

The analyzers may also be circumvented via the by-pass (117) if necessary.

The signals (135) and (136) produced by the analyzers (125) and (126) are processed in a computer (137) which produces a new signal (138) which in the simplest case directly affects the valve (100) which controls the air supply to the main gas flow.

Figure 2:
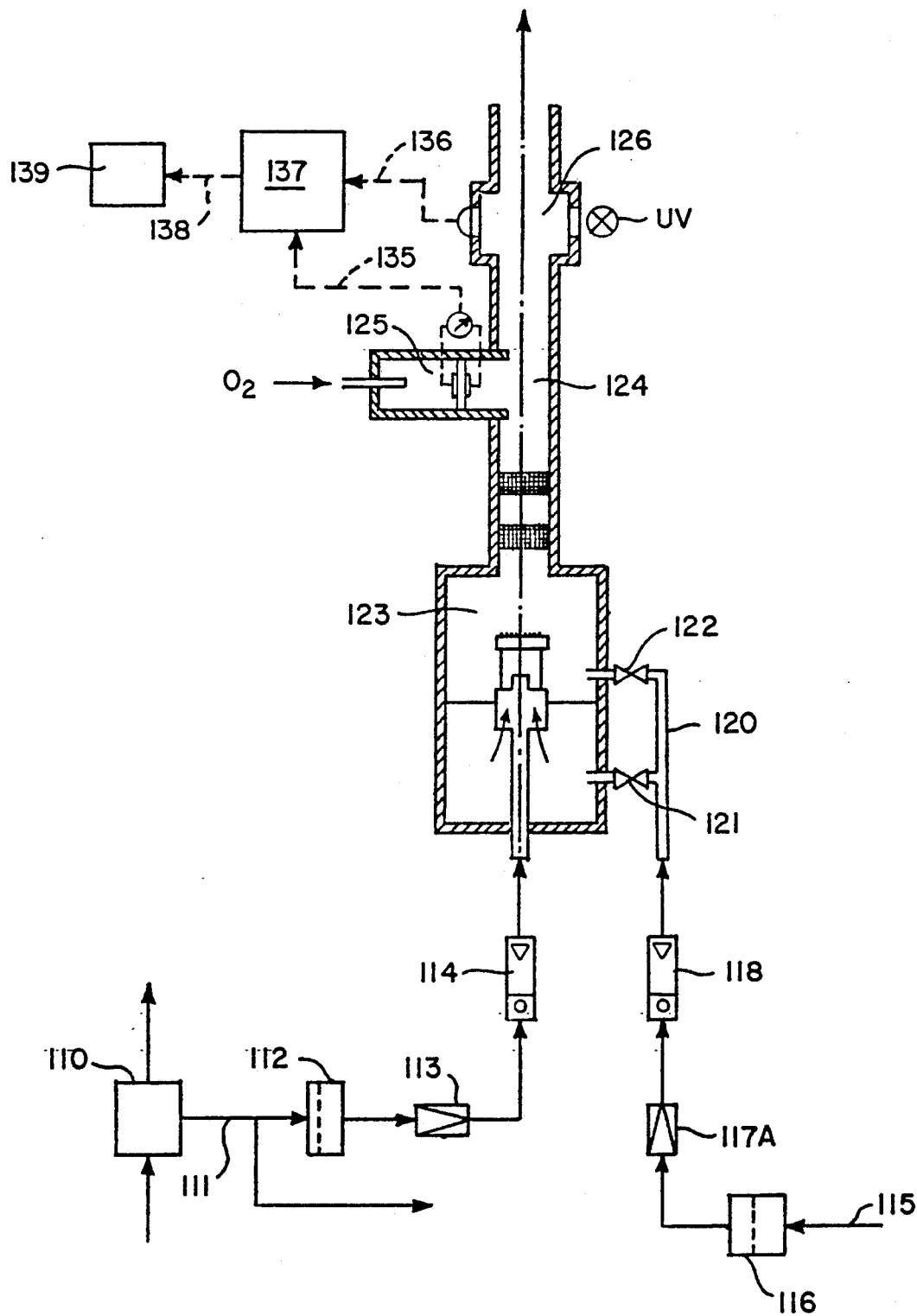

The preferred embodiment is explained in more detail by means of FIG. 2.

A gas sample (111) is taken from the main gas flow by means of the sampler (110). Sample taking takes place, for example, by utilizing the operating pressure necessary for the furnace 102 (FIG. 1) via a sample taking nipple which may be constructed as a filter probe with return blow device, but can also take place by means of a membrane or jet pump. Depending on the dust content and dew point of the analysis gases, it is conducted over appropriate drying filters (112). A pressure reducer (113) reduces the initial pressure of 0.3–1.8 bar to about 0.3 mb. A throughput regulator (114) sets a throughput rate of about 100 l/hr with an accuracy of ±1% but with a much higher short term reproducibility. The gas sample then arrives in the combustion furnace (123) which excels in acid gas resistance and quantitative combustion of the gas mixture. One combustion furnace is especially satisfactory as produced by the Apparatebau J. H. Reineki GmbH, Bochum under the designation WM.

The combustion air (115) arrives after passing through an oil and dust filter (116) via the pressure reducer (117A) which regulates the pressure to about 15 mn and the throughput regulator (118) which guarantees a throughput rate of about 1500 l/hr ±1% through the distributor line (120) and via the valves (121) and (122) in the combustion furnace (123). The air supply optimal for quantitative combustion is set with the valves (121) and (122).

An oxygen analyzer (125) is installed in the exhaust pipe (124) of the combustion furnace (123) which emits an analog signal (135) to a computer (microprocessor) (137). Electro-chemical measuring cells with solid electrolytes, for example, zirconium dioxide cells have been satisfactory as oxygen sensors. Other analyzers may also be used as long as they attain the high response speed of less than 10 seconds and a good short term reproducibility of at least 0.05% and withstand the high temperatures of the combustion gases of 600 to 800° C. The gas flow then passes through the second analyzer (126) in which the $SO_2$ concentration is measured by UV absorption. In order to guarantee a high signal availability of more than 99% UV photometers should be used which do not have movable parts in the detector system. Such an analyzer may be, for example, a Du Pont process photometer type PA 400. A second signal (136) is supplied to the computer (137) which after processing both signals (135) and (136), emits the analog control signal (138) to the process controller (139) which controls the adjusting element(s) responsible for regulation of the air flow to the Claus plant furnace.

Figure 3:
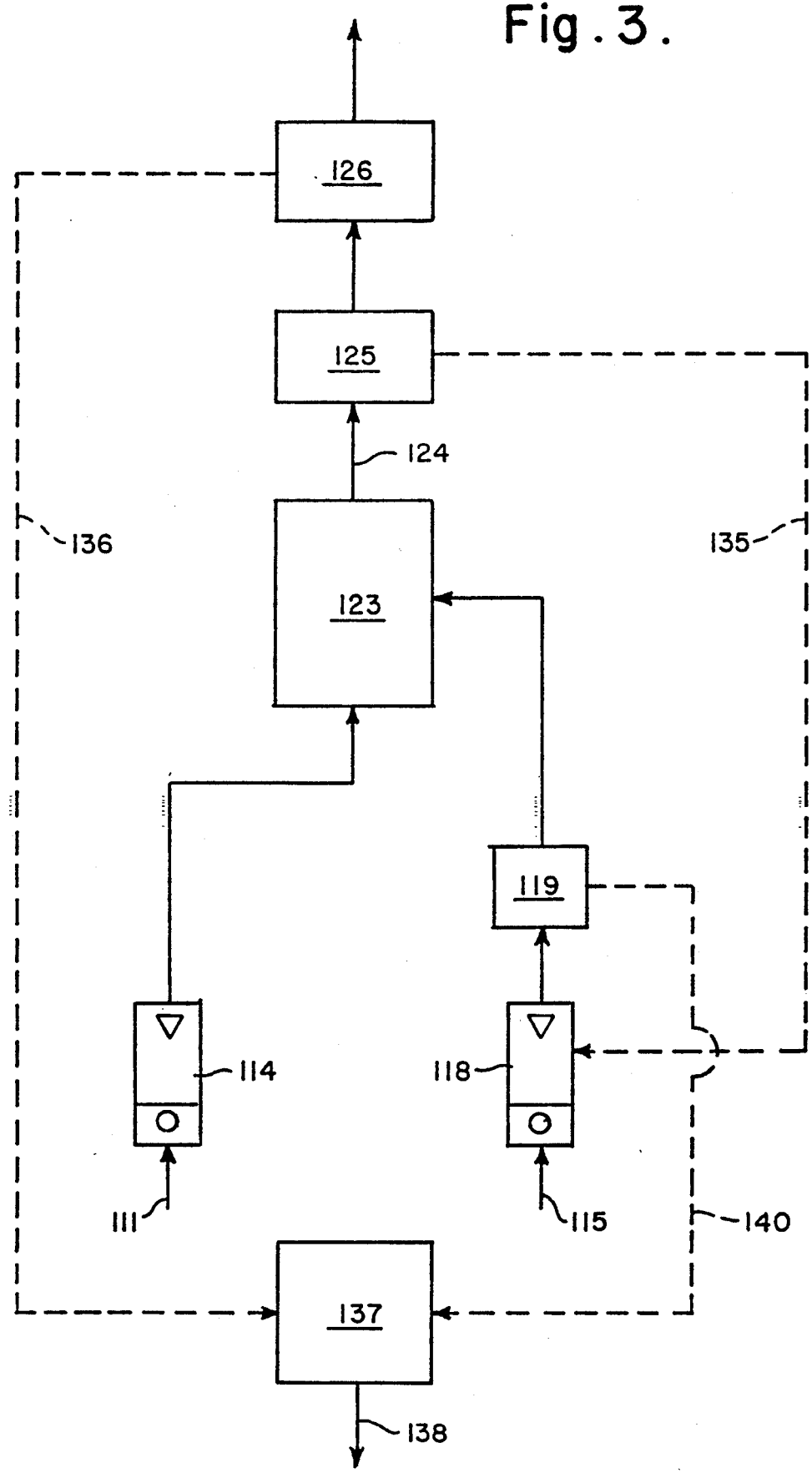
FIG. 3 is a further refinement of the method of the invention.

A further refinement possibility of the process according to the invention is shown in FIG. 3.

Instead of forwarding the oxygen excess signal (135) directly to the computer (137), the throughput regulator (118) is controlled with this signal (135) in such a way that only the stoichiometric oxygen amount enters the burner, the burner exhaust gas, therefore, does not any longer contain excess oxygen. A mass throughput meter (119) added to the throughput regulator (118)

then supplies the necessary second signal (140) to the computer (137).

In addition to the above described method according to the invention which allows a predetermination of the oxygen demand during rapid fluctuations in the gas composition, analysis instruments (108 in FIG. 1) are installed in the waste gas line (107 in FIG. 1) of the Claus installation, which determine the concentration of residual $H_2S$ and $SO_2$ so that long term deviations from the set value can be corrected. The Du Pont Photometer system type 4620 may be used, for example, which is equipped with two UV Photometers type PA 400 for the analysis in the waste gas line.

All relevant changes in the feed gas composition can be detected and yield the accurate analog control signal for oxygen feed demand as a result of the relevant feed gas composition change. For example, an increase in $H_2S$ concentration in the feed gas results not only in a lower oxygen analyzer signal but also in a higher $SO_2$ concentration signal. Hence, the analog oxygen demand signal from the computer acting on these two signals will increase only to the extent required to oxidize $\frac{1}{3}$ of the increased $H_2S$ concentration However, an increase in hydrocarbon or hydrogen contents would result only in a lower oxygen analyzer signal without any significant change in the $SO_2$ concentration signal. The computer then provides a new oxygen demand signal required to completely oxidize the increased hydrocarbon and hydrogen concentrations.

A further decisive advantage of the method in addition to its simplicity is the speed and accuracy with which short term changes in the gas composition can be followed up. A change in the composition of the operation gas can be detected, analyzed and responded to within ten seconds.

This was even more surprising since it could be expected that, by connecting the individual components of the analyzer system in series, an addition of individual errors could also occur leading to insufficient accuracy in the air demand determination. For example, the throughput regulators for the mass flow regulation of the sample gas and combustion air placed before the combustion furnace are affected with an inaccuracy of about $\pm 0.5\%$ each. The efficiency of the combustion furnace in practice is limited to about 98%. In addition, the analyzers for $SO_2$ and $O_2$ have an error, for example, of $\pm 2\%$ of the appropriate measured range. The absolute error of the total system, in other words, of the linear air demand signal produced from the $SO_2$ and $O_2$ signals could attain 5 to 10% of the measured range by addition of all errors and additional consideration of atmospheric pressure fluctuations.

Surprisingly, however, a very high reproducibility is attained within a very short time (e.g. $\pm 0.05\%$ within about 10 minutes or $\pm 0.1\%$ within about 30 minutes), which allows the exact regulation of rapid fluctuations in the operation gas composition.

The deviations occurring over a longer period caused, among other, by a drifting of the analyzer system and changes in the process parameters of the Claus installation are detected in the waste gas of the Claus installation by means of a $H_2S/SO_2$ ratio analyzer system, for example, the Du Pont analyzer system 4620 and are accordingly considered. An optimum regulation for a period depending, among other, on the catalyst retention time and the ratio of installation throughput/capacity will, therefore, give priority to the air demand signal delivered by the method according to the invention and eliminate long term trends by means of the waste gas analyzer.

I CLAIM:

1. In the method for the combustion of hydrogen sulfide containing gas mixtures for sulfur recovery and gas purification by burning the gas mixture in a furnace with oxygen, wherein the improvement comprises;
   (1) continuously and rapidly predetermining and monitoring the oxygen demand of the gas mixture by continuously removing a sample of the gas mixture before being fed into the furnace and rapidly feeding the sample into a second test furnace with at least a stoichiometric amount of oxygen and completely burning the sample of the gas mixture;
   (2) continuously analyzing the resulting burned sample gas mixture by passing the burned mixture into analysis instruments that measure the oxygen and sulfur dioxide content of the burned sample mixture, said instrument each generating an output signal;
   (3) feeding the output signals to a computer which uses the output signals independently to calculate and generate an output signal indicative of the amount of oxygen needed for the burning of the gas mixture and
   (4) controlling a regulator that feeds oxygen to the furnace for the burning of the gas mixture by having the regulator receive the output signal from the computer thereby accurately regulating the amount of oxygen being fed to the furnace for the complete combustion of the gas mixture.

2. The method of claim 1 in which the analysis instruments comprise a continuously operating electrochemical measuring cell with solid electrolytes for the determination of the oxygen content of the burned gas mixture and a continuously operating ultraviolet light photometer for the determination of the sulfur dioxide content of the burned gas mixture.

* * * * *

UNITED STATES PATENT AND TRADEMARK OFFICE
CERTIFICATE OF CORRECTION

PATENT NO. : 5,008,203
DATED : April 16, 1991
INVENTOR(S) : Manfred Mathews It is certified that error appears in the above-identified patent and that said Letters Patent is hereby corrected as shown below:

Column 1 Line 67 "chromatographs" should read --chromatography--.

Column 3 Line 55 "(11)" should read --(111)--.

Column 3 Line 57 "(11))" should read --(110)--.

Column 3 Line 60 "(11) should read --(118)--.

Signed and Sealed this

Twenty-third Day of November, 1993

Attest:

BRUCE LEHMAN

*Attesting Officer*    *Commissioner of Patents and Trademarks*